(12) United States Patent
Williams

(10) Patent No.: US 12,280,096 B2
(45) Date of Patent: Apr. 22, 2025

(54) TREATMENTS OF CANCER USING NITROUS OXIDE AND BOTULINUM TOXIN

(71) Applicant: Penland Foundation, Beaumont, TX (US)

(72) Inventor: Roland M. Williams, Beaumont, TX (US)

(73) Assignee: Penland Foundation, Beaumont, TX (US)

( * ) Notice: Subject to any disclaimer, the term of this patent is extended or adjusted under 35 U.S.C. 154(b) by 255 days.

(21) Appl. No.: 17/862,269

(22) Filed: Jul. 11, 2022

(65) Prior Publication Data

US 2023/0009875 A1   Jan. 12, 2023

Related U.S. Application Data

(60) Provisional application No. 63/220,951, filed on Jul. 12, 2021.

(51) Int. Cl.
*A61K 38/48* (2006.01)
*A61K 9/00* (2006.01)
*A61K 31/04* (2006.01)

(52) U.S. Cl.
CPC ........ *A61K 38/4893* (2013.01); *A61K 9/0021* (2013.01); *A61K 31/04* (2013.01)

(58) Field of Classification Search
CPC ... A61K 38/4893; A61K 9/0021; A61K 31/04
See application file for complete search history.

(56) References Cited

U.S. PATENT DOCUMENTS

| | | |
|---|---|---|
| 6,063,768 A | 5/2000 | First |
| 6,500,436 B2 | 12/2002 | Donovan |
| 7,235,584 B2 | 6/2007 | Garzon et al. |
| 8,372,976 B2 | 2/2013 | Mortensen et al. |
| 8,399,401 B2 | 3/2013 | Foster et al. |
| 8,697,066 B2 | 4/2014 | Gaylis et al. |
| 9,243,301 B2 | 1/2016 | Foster et al. |
| 9,579,299 B2 | 2/2017 | Glozman |
| 9,945,856 B2 | 4/2018 | Van Der Hoek |
| 10,064,921 B2 | 9/2018 | Blumenfeld |
| 10,201,565 B2 | 2/2019 | Mailova et al. |
| 10,245,305 B2 | 4/2019 | First |
| 10,857,382 B2 | 12/2020 | Ibrahim et al. |
| 11,065,218 B2 | 7/2021 | Bannister et al. |
| 2002/0185126 A1 | 12/2002 | Krebs |
| 2005/0020654 A1 | 1/2005 | Pershadsingh et al. |
| 2005/0152905 A1 | 7/2005 | Omoigui |
| 2005/0267009 A1 | 12/2005 | Deagle |
| 2006/0178354 A1 | 8/2006 | Lucas |
| 2009/0071481 A1 | 3/2009 | Fishman |
| 2009/0232849 A1 | 9/2009 | Gallez et al. |
| 2009/0324678 A1 | 12/2009 | Thorne et al. |
| 2012/0207733 A1 | 8/2012 | Jacky et al. |
| 2012/0207742 A1 | 8/2012 | Jacky et al. |
| 2013/0095194 A1 | 4/2013 | Bessiere et al. |
| 2013/0177548 A1 | 7/2013 | Shaari |
| 2013/0302445 A1 | 11/2013 | Barbut et al. |
| 2015/0197739 A1 | 7/2015 | James et al. |
| 2016/0067276 A1 | 3/2016 | Polizzotti et al. |
| 2016/0243232 A1 | 8/2016 | Pickett |
| 2017/0049866 A1 | 2/2017 | Sanders |
| 2017/0136105 A1 | 5/2017 | Ho et al. |
| 2017/0246267 A1 | 8/2017 | Wang et al. |
| 2018/0235931 A1 | 8/2018 | Basta et al. |
| 2018/0243373 A1 | 8/2018 | Hamed |
| 2018/0296582 A1 | 10/2018 | Von Maltzahn et al. |
| 2018/0296732 A1 | 10/2018 | Kutryk |
| 2019/0127718 A1 | 5/2019 | Madec et al. |
| 2019/0185837 A1 | 6/2019 | Jacky et al. |
| 2019/0298779 A1 | 10/2019 | Falb et al. |
| 2019/0314470 A1 | 10/2019 | Khavari et al. |
| 2019/0315836 A1 | 10/2019 | Delahay |
| 2020/0046813 A1 | 2/2020 | Borodic |
| 2020/0056145 A1 | 2/2020 | Brown et al. |
| 2020/0360483 A1 | 11/2020 | Dong et al. |
| 2020/0368365 A1 | 11/2020 | Ruoslahti et al. |
| 2021/0121541 A1 | 4/2021 | Brin et al. |
| 2021/0130445 A1 | 5/2021 | Brin |
| 2021/0177823 A1 | 6/2021 | Weinstein et al. |
| 2021/0177946 A1 | 6/2021 | Sanders |
| 2021/0205415 A1 | 7/2021 | Shandler et al. |
| 2021/0205422 A1 | 7/2021 | Kalinichev et al. |

(Continued)

FOREIGN PATENT DOCUMENTS

| | | |
|---|---|---|
| AU | 2011203062 | 1/2013 |
| CN | 101031317 | 7/2012 |
| CN | 105147608 | 12/2015 |

(Continued)

OTHER PUBLICATIONS

Jung et al. (Korean Journal of Anesthesiology vol. 58 No. 1, pp. 61-69).*
Koblin (Seminars in Surgical Oncology vol. 6 No. 3, pp. 141-147).*
Lassen and Kristensen, "Remission in Chronic Myeloid Leucemia Following Prolonged Nitrous Oxide Inhalation," Danish Medical Bulletin, vol. 6, No. 8, pp. 252-255 (1959).
Aguirre-Siancas, "Substance p. proinflammatory cytokines, transient receptor potential vanilloid subtype 1 and COVID-19: a working hypothesis," Neurología, 36, pp. 169-189 (2021).
Australian Dental Association, "The Use of Nitrous Oxide During COVID-19," available online at <https://www.ada.org.au/Covid-19-Portal/Cards/Misc/Infection-Control-Cards/The-Use-of-Nitrous-Oxide-During-COVID-19>, 2 pages (2020).

(Continued)

*Primary Examiner* — Robert A Zeman

(74) *Attorney, Agent, or Firm* — Fox Rothschild LLP

(57) ABSTRACT

Embodiments of the disclosure are related to a method of treating cancer including preventative treatment comprising administering nitrous oxide and oxygen to the patient by inhalation, and/or administering a botulinum toxin to the patient by injection, wherein the latter is directed to preventative treatment.

7 Claims, No Drawings

(56) References Cited

U.S. PATENT DOCUMENTS

2021/0252033 A1  8/2021  Painter et al.

FOREIGN PATENT DOCUMENTS

| | | |
|---|---|---|
| EP | 1187635 | 2/2004 |
| EP | 1807118 | 7/2007 |
| EP | 1890714 | 2/2008 |
| EP | 1919892 | 5/2008 |
| EP | 2012811 | 1/2009 |
| EP | 2200999 | 6/2010 |
| EP | 2610244 | 7/2013 |
| EP | 2279196 | 1/2015 |
| EP | 2985281 | 2/2016 |
| EP | 2667854 | 1/2019 |
| EP | 3689331 | 8/2020 |
| KR | 20170014106 | 2/2017 |
| WO | 0155304 | 8/2001 |
| WO | 0276177 | 10/2002 |
| WO | 2005009437 | 2/2005 |
| WO | 2006018655 | 2/2006 |
| WO | 2008064552 | 6/2008 |
| WO | 2014/053651 | 4/2014 |
| WO | 2018/129404 | 7/2018 |
| WO | 2019051380 | 3/2019 |
| WO | 2019075263 | 4/2019 |
| WO | 2019191752 | 10/2019 |
| WO | 2020010123 | 1/2020 |
| WO | 2020065249 | 4/2020 |
| WO | 2020117564 | 6/2020 |
| WO | 2020218823 | 10/2020 |
| WO | 2021101902 | 5/2021 |
| WO | 2021113311 | 6/2021 |
| WO | 2021163222 | 8/2021 |

OTHER PUBLICATIONS

Fleischmann, "Nitrous oxide may not increase the risk of cancer recurrence after colorectal surgery: a follow-up of a randomized controlled trial," BMC Anesthesiology, (2009).

International Search Report and Written Opinion for International Patent Application No. PCT/US2022/036729, mailed Nov. 15, 2022 (12 pages).

Ishikawa, "Nitrous Oxide Decreases Substance p. Receptor Binding in The Rat Spinal Cord," Journal of Neurosurgical Anesthesiology, 1(4), pp. 316-322 (1989).

Turan et al., "Nitrous Oxide for the Treatment of Chronic Low Back Pain," Anesthesia & Analgesia, 121(5), pp. 1350-1359 (2015).

Lichtigfeld et al., "The treatment of alcoholic withdrawal states with oxygen and nitrous oxide," South African Medical Journal, 61(349), pp. 349-351 (1982).

Lotz et al., "Effects of inhaled nitric oxide in COVID-19-induced ARDS—Is it worthwhile?" Acta Anaesthesiol. Scand., 65, pp. 629-632 (2021).

Manigandan et al., "A review on role of nitrous oxide nanoparticles, potential vaccine targets, drug, health care and artificial intelligence to combat COVID-19," Applied Nanoscience, 8 pages (2021).

Mehboob, "Aprepitant as a combinant with Dexamethasone reduces the inflammation via Neurokinin 1 Receptor Antagonism in severe to critical Covid-19 patients and potentiates respiratory recovery: A novel therapeutic approach," 13 pages (2020).

Miller et al., "Inhalational Anesthetic," StatPearls Publishing, Treasure Island (FL); 10 pages (2021).

Wiley, "Use of nitrous oxide- oxygen inhalation sedation in the COVID- 19 era," Int. J. Paediatr. Dent., 31, pp. 433-435 (2021).

Molina et al., "Nitrous oxide inhalant abuse and massive pulmonary embolism in COVID-19," American Journal of Emergency Medicine, 38(7), 2 pages. 1549.e1-1549.e2 (2020).

National Cancer Institute, "Cancer Pain (PDQ®)-Health Professional Version," available online at <https://www.cancer.gov/about-cancer/treatment/side-effects/pain/pain-hp-pdq>; Updated Sep. 2, 2022, 89 pages.

National Cancer Institute, "Nitric Oxide Releasing Solutions to Prevent and Treat Mild/Moderate COVID-19 Infection (NOCOVID)," available online at <https://clinicaltrials.gov/ct2/show/NCT04337918>; First Posted: Apr. 8, 2020; Last Update Posted: Feb. 10, 2021, (11 pages).

Nowaczyk et al., "Carbon Monoxide and Nitric Oxide as Examples of the Youngest Class of Transmitters," Int. J. Mol. Sci., 22(6029), 25 pages (2021).

Park et al., "Cytokine Balance in the Lungs of Patients with Acute Respiratory Distress Syndrome," American Journal of Respiratory and Critical Care Medicine, 164(10), pp. 1896-1903 (2011).

Patyar et al., "Bacteria in cancer therapy: a novel experimental strategy," Journal of Biomedical Science vol. 17 (21), 9 pages (2010).

Rao et al., "Comparison of five equations for estimating resting energy expenditure in Chinese young, normal weight healthy adults," European Journal of Medical Research, 17(26), pp. 1-9 (2012).

Takasusuki et al., "Effects of General Anesthetics on Substance P Release and c-Fos Expression in the Spinal Dorsal Horn," Anesthesiology, 119, pp. 433-442 (2013).

\* cited by examiner

TREATMENTS OF CANCER USING NITROUS OXIDE AND BOTULINUM TOXIN

PRIORITY CLAIM

This application is based on and claims under 35 U.S.C. § 119(a) the benefit of U.S. Provisional Application No. 63/220,951, filed Jul. 12, 2021, the entirety of which is incorporated by reference.

This application is also related by ownership to the following cases, filed on Oct. 18, 2019: TREATMENT OF AUTISM USING BOTULINUM TOXINS, Ser. No. 16/657,933, now U.S. Pat. No. 10,722,552; filed on Oct. 18, 2019: TREATMENT OF NARCOTICS TOLERANCE USING BOTULINUM TOXINS, Ser. No. 16/657,950, now abandoned; filed on Aug. 17, 2020: TREATMENT METHODS USING BOTULINUM TOXINS, Ser. No. 16/995,042, now U.S. Pat. No. 11,241,479; filed on May 15, 2020: TREATMENT OF DYSLEXIA USING BOTULINUM TOXIN, Ser. No. 16/875,912, now U.S. Pat. No. 10,967,052; filed on Aug. 17, 2020: TREATMENT OF ASTHMA USING BOTULINUM TOXIN, Ser. No. 16/995,042, now U.S. Pat. No. 11,241,479; filed on May 15, 2020: TREATMENT OF CHRONIC OBSTRUCTIVE PULMONARY DISEASE USING BOTULINUM TOXIN, Ser. No. 16/875,935, now U.S. Pat. No. 10,987,411; filed on May 15, 2020: TREATMENT OF CARDIAC ARRHYTHMIA USING BOTULINUM TOXIN, Ser. No. 16/875,945, now U.S. Pat. No. 10,960,060; filed on May 15, 2020: TREATMENT OF CIRRHOSIS USING BOTULINUM TOXIN, Ser. No. 16/875,951, now U.S. Pat. No. 11,090,371; filed on May 4, 2022: TREATMENT OF ARDS AND OTHER CONDITIONS CAUSED BY ACUTELY ELEVATED CYTOKINE LEVELS AND POST ARDS CHRONIC CYTOKINE PRODUCTION USING INHALED ANESTHETICS, Ser. No. 17/662,068.

TECHNICAL FIELD

Embodiments of the present disclosure generally relate to the treatment of cancer and treatment to prevent cancer.

DESCRIPTION OF RELATED ART

Cancer is a leading cause of deaths worldwide. Diagnostic procedures, in some cases, begin only after a patient is already present with symptoms, leading to costly, invasive, and time-consuming procedures. In addition, inaccessible areas sometimes prevent an accurate diagnosis. Further, high cancer morbidities and mortalities are associated with late diagnosis.

SUMMARY

Embodiments of the disclosure are related to a method of treating cancer by mitigating acute overactivation of a cytokine system, in a patient in need thereof. The method comprises administering nitrous oxide and oxygen to the patient by inhalation, before, during, and/or after the cancer occurs, thereby treating the cancer. Embodiments include method of preventative treatment of cancer comprising administering a botulinum toxin to the patient by injection.

In some embodiments, a composition of the nitrous oxide and oxygen may be from about 1% nitrous oxide/about 99% oxygen to about 70% nitrous oxide/about 30% oxygen; from about 40% nitrous oxide/about 60% oxygen to about 50% nitrous oxide/about 50% oxygen; or about 50% nitrous oxide/about 50% oxygen. The nitrous oxide and oxygen may be administered to an adult who weighs about 150 lbs. for about between 1 minute and about 1 hour every about 4-6 hours; or for about 20 minutes every about 4-6 hours. The nitrous oxide and oxygen may be administered by continuous administration over the period of time. A composition, duration, interval, and total amount of the inhaled anesthetics provided to an adult or a child may be adjusted for age, weight, or a combination thereof.

In some embodiments, the botulinum toxin may be selected from the group consisting of botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, and a combination thereof.

In some embodiments, the botulinum toxin may be administered by subcutaneous or intradermal injection, 1-4 units to and/or around the vicinity of a trigeminal nerve, 1-4 units to and/or around the vicinity of a cervical nerve, lateral to the patient's spine, 1-4 units to and/or around the vicinity of a thoracic nerve, lateral to the spine, 1-4 units to and/or around the vicinity of a lumbar nerve, lateral to the spine, and/or 1-4 units to and/or around the vicinity of a sacral nerve, lateral to the spine. A total dosage of the botulinum toxin in an adult who weighs about 150 lbs may be less than or equal to about 50 units (about 1 to 50 units inclusive of endpoints), and the total dosage of the botulinum toxin in an adult may be adjusted for weight. A total dosage of the botulinum toxin in a child over about 5 years old and a toddler about from 1 to 5 years old may be adjusted for age, weight or a combination thereof. Each of the subcutaneous or intradermal injections may be bilateral.

The trigeminal nerve may be selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve and a combination thereof. The cervical nerve may be selected from the group consisting of a c-2 nerve, c-3 nerve, c-4 nerve, c-5 nerve, c-6 nerve, c-7 nerve, c-8 nerve and a combination thereof. The thoracic nerve may be selected from the group consisting of a t-2 nerve, t-3 nerve, t-5 nerve, t-6 nerve, t-7 nerve, t-8 nerve, t-9 nerve, t-10 nerve, t-11 nerve, t-12 nerve and a combination thereof. The lumbar nerve may be selected from the group consisting of a 1-1 nerve, 1-2 nerve, 1-3 nerve, 1-4 nerve, 1-5 nerve and a combination thereof. The sacral nerve may be selected from the group consisting of a s-1 nerve, s-2 nerve, s-3 nerve, s-4 nerve, s-5 nerve and a combination thereof.

Also disclosed is method of treating cancer and/or post-cancer symptoms or any condition that remains after acute overactivation of a cytokine system, in a patient in need thereof. The method comprises administering nitrous oxide and oxygen to the patient by inhalation, thereby treating the cancer and/or post-cancer symptoms or conditions. Post-cancer symptoms or conditions means symptoms or conditions arising from or caused once cancer has formed and harmful side effects of cancer treatments.

In some embodiments, a composition of the nitrous oxide and oxygen may be from about 1% nitrous oxide/about 99% oxygen to about 70% nitrous oxide/about 30% oxygen; from about 40% nitrous oxide/about 60% oxygen to about 50% nitrous oxide/about 50% oxygen; or about 50% nitrous oxide/about 50% oxygen. The nitrous oxide and oxygen may be administered to an adult who weighs about 150 lbs. for about between 1 minute and about 1 hour every about 4-6 hours; or for about 20 minutes every about 4-6 hours. The nitrous oxide and oxygen may be administered by continuous administration over the period of time. A composition, duration, an interval, and a total amount of the inhaled anesthetics provided to an adult or a child may be adjusted for age, weight, or a combination thereof.

In some embodiments, the botulinum toxin may be selected from the group consisting of botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, and a combination thereof.

In some embodiments, the botulinum toxin may be administered by subcutaneous or intradermal injection, 1-4 units to and/or around the vicinity of a trigeminal nerve, 1-4 units to and/or around the vicinity of a cervical nerve, lateral to the patient's spine, 1-4 units to and/or around the vicinity of a thoracic nerve, lateral to the spine, 1-4 units to and/or around the vicinity of a lumbar nerve, lateral to the spine, and/or 1-4 units to and/or around the vicinity of a sacral nerve, lateral to the spine. A total dosage of the botulinum toxin in an adult who weighs about 150 lbs may be less than or equal to about 50 units, and the total dosage of the botulinum toxin in an adult may be adjusted for weight. A total dosage of the botulinum toxin in a child over about 5 years old and a toddler about from 1 to 5 years old may be adjusted for age, weight or a combination thereof. Each of the subcutaneous or intradermal injections may be bilateral.

The trigeminal nerve may be selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve and a combination thereof. The cervical nerve may be selected from the group consisting of a c-2 nerve, c-3 nerve, c-4 nerve, c-5 nerve, c-6 nerve, c-7 nerve, c-8 nerve and a combination thereof. The thoracic nerve may be selected from the group consisting of a t-2 nerve, t-3 nerve, t-5 nerve, t-6 nerve, t-7 nerve, t-8 nerve, t-9 nerve, t-10 nerve, t-11 nerve, t-12 nerve and a combination thereof. The lumbar nerve may be selected from the group consisting of a 1-1 nerve, 1-2 nerve, 1-3 nerve, 1-4 nerve, 1-5 nerve and a combination thereof. The sacral nerve may be selected from the group consisting of a s-1 nerve, s-2 nerve, s-3 nerve, s-4 nerve, s-5 nerve and a combination thereof.

Embodiments of the present disclosure may, but not be limited to, 1) treat and mitigate the severe pain associated with some malignant cancers, 2) treat and mitigate the extreme cytokine production cytokine release syndrome produced during some cancer treatments, 3) treat and mitigate the cytokine release by some malignant tumors which damage the host, 4) treat and mitigate the intratumor production of cytokines which inhibit host immune response and the effectiveness of chemotherapy, and 5) treat and mitigate the malignancy and ability of a tumor to metastasize. Embodiments of the present disclosure may be related to mitigating or controlling the chronic substance P initiated cytokine release causing a chronic inflammatory condition in many tissues and organs. This chronic inflammation may initiate cancerous changes in cells and tumor development.

DETAILED DESCRIPTION

Further in relation to this, before explaining at least the preferred embodiments of the disclosure in greater detail, it is to be understood that the disclosure is not limited in its application to the details of construction and to the arrangements of the components set forth in the following description. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, "consists essentially of" when used in conjunction with a composition, a nitrous oxide composition, means excluding other materials that contribute to mitigating cytokine overproduction, thereby treating cancer or post-cancer symptoms. The objective of administering nitrous oxide and oxygen by inhalation is to treat cancer or post-cancer symptoms by mitigating cytokine overproduction. With the language, other materials that contribute to the treatment that materially affect the basic and novel characteristics of embodiments of the present disclosure are not required and are potentially counterproductive because they may offset the treatment effect of nitrous oxide and oxygen. In other words, the meaning of "consists essentially of" is tied to the objective and excludes materials (that contribute to the treatment) that are pharmaceutically active for the treatment and materially mitigate cytokine overproduction and thereby affecting the treatment of cancer or post-cancer symptoms. Small traces that have little or no effect to the treatment as part of the embodiments of the present disclosure may exist in a composition that consists essentially of nitrous oxide and oxygen under the definition because it would not materially affect its function and/or objective. As described, the objective when using the botulinum toxin treatment is to use the botulinum toxin to prevent cancer, a preventative treatment and the objective when using the nitrous oxide treatment is to use the nitrous oxide to treat cancer symptoms and/or post-cancer symptoms and conditions.

As used herein, "consists essentially of" when used in conjunction with a composition, a botulinum toxin composition, means excluding other materials that contribute to preventing cancer or cancer formation. The objective of administering botulinum toxin is to treat conditions that cause cancer. With the language, other materials that contribute to the treatment that materially affect the basic and novel characteristics of embodiments of the present disclosure are not required. In other words, the meaning of "consists essentially of" is tied to the objective and excludes materials (that contribute to the treatment) that are pharmaceutically active for the treatment and materially mitigate cytokine overproduction and thereby affecting the preventative treatment. Small traces that have little or no effect to the treatment as part of the embodiments of the present disclosure may exist in a composition that consists essentially of botulinum toxin (as described herein) under the definition because it would not materially affect its function and/or objective.

As used herein, the term "about" means approximately or nearly and in the context of a numerical value or range set forth herein means±10% of the numerical value or range recited or claimed.

The term "treating" includes delaying, alleviating, mitigating, or reducing the intensity, progression, or worsening of one or more attendant symptoms of a disorder or condition and/or alleviating, mitigating, or impeding one or more causes of a disorder or condition. Treatment under the present disclosure may include preventative treatment including prophylactic treatment and remission treatment.

The term "therapeutically effective amount" or "therapeutically effective dose" refers to the amount of a composition, compound, therapy, or course of treatment that, when administered to an individual for treating a disorder or disease, is sufficient to affect such treatment for the disorder or disease. The "therapeutically effective amount" will vary depending on the composition, the compound, the therapy, the course of treatment, the disorder or disease and its severity and the age, weight, etc., of the individual to be treated.

The term "unit" refers to the amount of botulinum toxin needed to kill 50% of a group of 18-20 gm female Swiss-Webster mice given the injection intraperitoneally.

The term "vicinity of a nerve" refers to anywhere on the dermatome involved with the nerve.

Inhaled Anesthetics

An inhaled anesthetic is a chemical compound possessing general anesthetic properties that can be delivered by inhalation. Agents of current use include, but are not limited to, halothane, isoflurane, sevoflurane, desflurane, nitrous oxide, and xenon. There are dozens of other agents that currently have no current clinical use.

One of the mechanisms by which the inhaled anesthetics exert their sedative effects is by direct suppression of central pain and consciousness through the opioid receptors. Another clinical effect of the inhaled anesthetics is the suppression of the tachykinins—substance P, CGRP, and glutamate in the dorsal root and vagal ganglia. Since the half-life of the tachykinins is seconds to minutes, this effect is almost instantaneous. Studies show the inhaled anesthetics suppress the production of the tachykinins in the ganglia of the sensory nerves. In this location, the excess substance P, glutamate, and Calcitonin Gene Related Peptide (CGRP) are produced in the structural cells and also in the ganglia, satellite, glial, and astrocyte cells and released into the cerebrospinal fluid (CSF) around the neurons as well as intraneurally and released at the neuron terminal. This mechanism is part of the neural injury mechanism that releases glutamate to cause pain and increased symptoms and stimulates severe nausea. It also induces substance P to trigger immune responses to chronic irritation, or infection.

Studies as well as clinical observation has shown that about 30 minutes of nitrous oxide at 40%-50% nitrous oxide/50%-60% oxygen will almost instantly suppress the symptoms of conditions such as migraine, fibromyalgia, anxiety, trigeminal neuralgia, asthma, post-herpetic neuropathy, and neuropathy pain. These conditions are known to be caused by excess tachykinin production. The clinical observation of this suppression is that it can last for 4-6 hours after withdrawal from the nitrous oxide. Asthma is thought to be caused by chronic low-grade overproduction of substance P, resulting in hyper sensitization of the lung epithelium. Clinical observation has shown that nitrous oxide can cause suppression of all asthma symptoms for 4-6 hours. This indicates that the nitrous oxide not only stops the neural production of substance P, but also the epithelial production of substance P.

Increasing level of substance P is produced by malignant cancers and thought to initiate the cytokine reactions in the conditions that are being addressed in embodiments of the present disclosure. Nitrous oxide may be the best inhaled anesthetic to use in a clinical setting. It is fairly inert compared to most inhaled anesthetics. It does not depress respiration. It is readily available in a portable nitrous oxide/oxygen tank system that can accurately regulate volume, mixture, and flow rate. It has been used in general anesthesia and conscious sedation in the dental setting for over 100 years.

There are no toxic effects with short-term use. Longer term use can suppress folic acid levels which can cause damage to the nervous system. Supplemental folic acid should be able to eliminate this problem.

The use of nitrous oxide and oxygen may lower the ganglia and epithelial production of substance P. Other inhaled anesthetic may be used to suppress the production of substance dosages that do not cause over-sedation, respiratory depression, or irritation of the lungs or other side effects. The inhaled anesthetics must be safe for patients to inhale. Such inhaled anesthetics may include, but not be limited to, halothane, isoflurane, sevoflurane, desflurane, nitrous oxide, xenon, or a combination thereof. The inhaled anesthetics are sub-classified as either volatile or non-volatile. The volatile anesthetics (e.g., halothane, isoflurane, sevoflurane and desflurane) are liquids at room temperature and require the use of vaporizers for inhalational administration. The non-volatile anesthetics (e.g., nitrous oxide and xenon) are in gas form at room temperature. The inhaled anesthetics described in embodiments of the present disclosure do not encompass anesthetics (e.g., barbiturates, ketamine, propofol) administered by injections such as an intravenous injection.

The inhaled dosage of nitrous oxide and oxygen may be from about 1% nitrous oxide/about 99% oxygen to about 70% nitrous oxide/about 30% oxygen depending on individual needs and sensitivity. Clinical indications suggest that from about 40% nitrous oxide/about 60% oxygen to about 50% nitrous oxide/about 50% oxygen would be optimal. Other inhaled anesthetics may have to be used at a different oxygen % than the nitrous oxide to produce effective clinical results. Other aforementioned inhaled anesthetics may be included in the dosage or only the specified composition may be used. In some embodiments, time of inhalation would vary from about one minute to about one hour with about 30 minutes being the optimal time frame. Duration of substance P suppression may be from about 1 minute to about 12 hours with average cases of about 4-6 hours of substance P suppression. Depending on the level of substance the nitrous oxide and oxygen may be administered to a patient before, during, and/or after ARDS occurs between about for about 1 minute to about 12 hours every about 4-6 hours and optionally with continuous administration over the period of time. The nitrous oxide/oxygen mechanism is suppression of substance P in the peripheral ganglia.

In general, a composition, a duration, an interval, and a total amount of the inhaled nitrous oxide and oxygen administered to an adult, or a child is adjusted for age, weight, or a combination thereof. In particular, the amount of nitrous oxide used, duration of inhalation, and length of effectiveness will have to be titrated to the individual. For example, adjustments will have to be made for age and body weight.

Mechanism of Botulinum Toxin

Botulinum toxins cleave and destroy a protein called synaptosomal nerve-associated protein 25 ("SNAP25") and/or synaptobrevin (also called vesicle-associated membrane protein ["VAMP"]). Botulinum toxin types A, C, and E cleave SNAP25 at different locations, but the effect is in general the same—the protein is destroyed and cannot function until the cell makes new ones. Botulinum toxin types B, D, F and G cleave VAMP present at the cytoplasmic surface of the synaptic vesicle. The two important locations in the body where the SNAP25 protein is found are at the terminals of the motor neurons (muscle) and in the cell membrane of astrocytes, glial cells, and satellite cells. These three cell types surround sensory neurons and form part of the blood-brain barrier. In motor nerves, vesicles of acetylcholine move from inside the motor neuron across the cell membrane at the synapse between the motor nerve and muscle fiber. SNAP25 is the protein used to accomplish this. Acetylcholine is released into the synapse and activates receptors in the muscle fiber, which contracts the muscle fiber. In sensory nerves, when a nerve is damaged from physical or mental injuries, the three aforementioned structural cells produce large amounts of substance P, (CGRP), and glutamate internally and the molecules are moved by vesicles to the cell membrane where the SNAP25 and/or VAMP moves the molecules through the cell membrane and releases the molecules into the cerebrospinal fluid that surrounds the neurons. There, the molecules of glutamate bind to the receptor on the sensory nerves, causing the neuro excitatory effects and substance P binds to NK-1 receptor on immune cells which activates them to release cytokines. The molecules of glutamate and substance P can also diffuse into the cerebral spinal fluid, migrate up and down the spinal cord, and influence other sensory nerves and immune cells to become hyperactive, a process called central sensitization.

This mechanism of cleaving the SNAP25 and/or VAMP or preventing vesicle transportation in muscles and sensory nerves causes the only known clinical effects of botulinum. Paralysis of muscles in the motor system lasts for 3-4 months until the cell grows a new protein. This effect has been used safely and effectively for decades for overactive muscles (such as to treat overactive muscles as part of cervical dystonia, blepharospasm, tic, Parkinson's, cerebral palsy, etc.), wrinkles in the face, excessive sweating, and overactive bladder.

In the sensory nerves, the mechanism has been used for treating migraines and depression. The effect of blocking the SNAP25 and/or VAMP in the glial, satellite, and astrocyte cells will work for 2-5 months until these cells grow new proteins. The important part of this mechanism is that the botulinum effect does not destroy the neural cells and does not stop the normal production of or effects of substance P, CGRP, or glutamate in sensory nerves. This mechanism gives a huge advantage over a monoclonal antibody which would eliminate all glutamate, CGRP, and substance P. Side effects of such elimination would be disastrous. The receptor antagonists also have problems—for example, because the receptor antagonists are not site specific, they block glutamate, substance P, and CGRP everywhere. Too little glutamate, substance P, and CGRP is a problem, as well as too much. It is difficult to regulate oral or I.V. doses to obtain the correct level of reduction in areas that are too high in glutamate, substance P, and/or CGRP without over reduction in areas with normal levels.

Small doses of botulinum toxin injected into a specific muscle can cleave SNAP25 and VAMP to calm the muscle's overreaction or paralyze the muscle temporarily if desired. Or, if injected subcutaneously near unmyelinated sensory nerves, the botulinum toxin can stop the overproduction of the sensory neuro excitatory compounds without affecting normal glutamate, substance P, and CGRP production and function. It is, however, noted that botulinum toxin is highly lethal. Botulinum toxin is the most toxic poison known. One molecule of botulinum toxin destroys one protein molecule of SNAP25 and/or VAMP. A little bit goes a long way. Its production, storage and injection must be done with knowledge and care.

In particular, the mechanism of the sensory effect (stopping overproduction of glutamate, substance P, and CGRP) is as follows: almost all nerves in the human body are surrounded by a protective coating called myelin, which protects the nerve and makes neural conduction faster. Botulinum toxin has difficulty penetrating the myelin. Just Under the skin are sensory pain nerves called C-fibers, which are unmyelinated. Research has shown that very low dose botulinum toxin can penetrate these axons and diffuse up the axon to the cell body into the CSF and affect the SNAP25 and/or VAMP on the glial, satellite, and astrocyte cells. Subsequently, botulinum toxin destroys the SNAP25 and/or VAMP proteins and prevents the release of the excess substance P, CGRP, and glutamate, which is involved in a response mechanism to neural injury without affecting normal glutamate, substance P, and CGRP production, use, or receptors elsewhere in the body. An Example of a malfunction with the normal nerve injury mechanism is an infection of a nerve by the shingles virus. The infection by the shingles virus damages the nerve but does not kill it, or there would be no feeling (numbness). This causes a spike in the production of glutamate, substance P, and CGRP. This causes the well-known shingles pain and hypersensitivity. Over a 2-3-month period, the infection is controlled, the nerve heals, and the overproduction of the neuro excitatory chemicals gets back to normal. However, sometimes for unknown reasons, the overproduction does not get back to normal but remains high, and severe chronic pain and hypersensitivity persists. Chronically over stimulated neurons can cause numerous problems depending on where the neurons are located. The neuro excitatory chemicals can travel up the spinal cord to the brain in the CSF and affect neurons there. This process is called central sensitization. Depending on where glutamate, substance P, and CGRP are produced and where the molecules travel to, the molecules can cause chronic pain, headaches, vertigo, sensitivity to light, sensitivity to touch, cold sensitivity, overactive bladder, depression, anxiety, flashbacks, mental fogginess, vasoconstriction of extremities, sleep disturbances. The overproduction of substance P can result in chronic inflammatory condition in the structure that the nerves innervate.

Cytokine Storm

Cytokines are a diverse group of small proteins secreted by cells that among other things regulate and participate in the inflammatory response. The major types are interferon's, interleukins, chemokines, colony-stimulating factors, and tumor necrosing factors.

The cytokine system is the first line of defense when a virus or bacterial attack occurs. It is also a major player in removing damaged or injured tissue and initiating the repair process. Some of the cytokines destroy damaged or defective cells, slow protein synthesis, damage DNA, have antiviral properties, and some suppress viral reproduction, and raise the body temperature. One of their functions is to slow an infection until the immune system produces antibodies to mark the virus or bacteria for destruction by other parts of the immune system. However, there is collateral damage to the body's cells from the cytokines. It is like chemotherapy for cancer; some normal tissues are damaged in the process of attacking the cancer. As the virus or bacteria is eliminated by the body, the production of the cytokines is slowed and eventually stops. The body repairs the damaged tissues by regeneration or fibrosis (replacement with scar tissue). Cytokine production stops. A patient recovers from the infection damaged tissue repaired or replaced with fibrosis tissue. Retained antibiotic memory is formed in case of later exposure to the same agent. This is immunity if recurrent exposure occurs then antibody production starts immediately.

Sometimes, when this system rids the body of the infection or removes dead or damaged tissue, the cytokine overproduction is not suppressed to normal, and the overproduction continues at an extreme level. This is called Cytokine Release Syndrome (cytokine storm). It is a lack of proper regulation of the immune system. The immune response flares out of control and can damage or kill the patient. The neuroexcitatory peptide substance P initiates this cytokine reaction. In cancer treatment, the destruction of large numbers of tumor cells by chemotherapy, radiation, or immunotherapy type treatments can trigger this dangerous Cytokine release syndrome. Cancers hijack parts of the normal cytokine reactions meant to fight infection and heal injury to survive the host immune response.

Prevention of Cancer

Chronic low-grade inflammation is thought to be one of the initiating factors in 80-90% of cancers. This inflammation occurs when factors such as, but not limited to smoking, infectious diseases, chronic alcohol use, environmental pollution, and obesity damage sensory neurons. This damage causes the neuro structural cells in their associated ganglia to produce and release substance P and glutamate in the chronically irritated area. These substances trigger the cytokine immune response. This system is a vital part of the mechanism to fight infection and heal damaged tissue. However, chronic exposure to these hundreds of kinds of cytokine molecules can result in damage and changes in normal cells. The cytokines can damage DNA and other structures in normal cells. It also inhibits a DNA repair mechanism called Non-homologous End Joining (NHEJ). This contributes to genome instability, induces uncontrolled reproduction, inhibits apoptosis pathways, and stimulates angiogenesis and neurogenesis. These are normal pathways used in fighting infections, healing wounds, and repairing damaged tissue. Chronic activation of these pathways can lead to damage and cancer-like changes in cells. Interestingly, chronic use of NSAIDs (anti-inflammatory drugs) has been shown to reduce cancer risk. The ability to control this chronic inflammation could prevent cancer initiation. Logically, controlling this chronic low-grade inflammation could prevent the formation of cancer cells.

Cancer

Cells with an abnormal growth tend to proliferate in an uncontrolled way and in some cases metastasize (spread to other parts of the body). It is a group of more than 100 different and distinct diseases. Cancer can involve any tissue of the body and have different forms in each tissue, depending on the cell type involved. Most cancers are named after the type of cell or organ of origin. If the cancer metastasizes, the new tumor bears the name of the original or primary tumor.

Cells become cancerous due to an accumulation of defects (mutations) in their DNA. These defects can result from inherited genetic defects, chronic infections, environmental factors (chemicals, pollution, etc.) or lifestyle choices such as heavy alcohol use, smoking, obesity, etc. There are billions of cells in the human body that die, become aged, defective, damaged, or cancerous every day. The body recognizes these cells and repairs or disposes of them in such a way as to not release toxic intracellular substances and cause inflammation. One mechanism is apoptosis. A defective cell recognizes something is wrong and releases a toxic substance that destroys itself (apoptosis). The immune system also recognizes these defective cells and destroys them preferably by immune cells that engulf and digest them rather than allowing the cells to lyse and spill their contents, causing inflammation. Cancer cells, because of their genetic aberrations, are recognized and destroyed just as bacteria, viruses, transplanted organs, cellular debris, and blood clots.

General Classification of Cancer

Even though human cancer cells are derived from normal cells, they are not even close genetically. Cancer cells have missing, broken, fused, extra, and translocated sections of chromosomes. They are classified under 3 broad categories 1) benign, 2) malignant, and 3) blood cells.

Benign Tumor

A benign tumor is an abnormal growth of cells that serves no purpose. It does not invade nearby tissue or spread to other parts of the body. In most cases, the outlook is very good. They can be serious if they press on vital structures such as nerves or blood vessels. Most times, they do not require treatment unless they cause problems. Causes can be environmental toxins, radiation, genetics, diet, stress, injury, inflammation, or infection. Treatment may be as simple as watching to make sure no problems develop, surgery, radiation, or medication. Genetic aberrations are present but a lot less severe and their genomes are much more stable than malignant cancers. They do not possess the characteristics of neurogenesis or angiogenesis. They do not possess increased levels of substance P and glutamate and therefore do not have increased levels of cytokines in or around them.

Malignant Cancer

Cells with genetic aberrations that can invade and kill nearby tissue can spread to other parts of the body. There are over 100 types of malignant cancers but no matter the tissue or cell type, they develop a series of common characteristics that allow them to survive and thrive:
 1. Seemingly uncontrolled reproduction
 2. Ability to evade the apoptosis mechanism
 3. Angiogenesis—the ability to induce blood vessels to grow to and into the tumor
 4. The inability to repair their DNA mutation and defects with NHEJ (Non-Homologous End Joining) and other mechanisms 5. The ability to avoid the immune system's mechanisms designed to detect and destroy them
6. The ability to survive the hypoxic, cytokine rich environment of the tumor
7. Neurogenesis—ability to induce neurons to grow to and into the tumor and/or produce neurons inside the tumor from stem cells
8. The ability to produce telomerase to repair Telomeres to prevent aging-induced senescence and apoptosis
9. Loss of or the inactivation of genes that are involved in the destruction of cancer cells, DNA repair mechanisms, then later the activation of genes or repair mechanisms of DNA to stabilize the cancer genome
10. Genetic adaptations to survive the hyperbaric hypoxic state in the tumor that results from inflammation producing slow infusion of nutrients and oxygen
11. Genetic adaptations to create, survive in, and use the cytokine-rich environment of the tumor Types of Tumors 1. Skin cancer—melanoma, basal cell, squamous, sebaceous, Merkel cell, etc.
2. Lung cancer—small cell, non-small cell, carcinoid, lymphomas, sarcomas, etc.
3. Blood cancer—(begin in the blood forming tissue, such as bone marrow, or in the cells of the immune system) broad classifications: leukemia, lymphomas, myelomas
4. Bone and muscle sarcomas
5. Brain/nervous system cancer—astrocytoma, glioblastoma, glioma, adenoma
6. Breast cancer—carcinomas
7. Endocrine system cancer—carcinoma, parathyroid cancer, thyroid, Merkel cell, etc.
8. Eye cancer—melanoma, blastoma
9. Gastrointestinal cancer—cholangiocarcinoma, carcinoid tumor, stromal tumor, pancreatic/islet cell
10. Genitourinary/gynecologic cancer—germ cell tumors, carcinoma, transitional cell.
11. Kidney, ovarian, prostate.
12. Head and neck cancer—pharyngeal cancers, esophageal, salivary gland, etc.
13. Thoracic/respiratory cancer—adenomas, carcinoids, mesothelioma, blastoma, small cell
14. Skin—basal cell, squamous cell, melanoma Current Treatments of Cancer Currently, there are 5 broad classifications of the current treatments of cancer:
1. Surgery—excision of all or parts of the tumor
2. Chemotherapy—chemicals or drugs that kill cancer cells. Most are antimetabolites that take advantage of the rapid uncontrolled growth of cancer as compared to normal cells. The cancer cells take in more of these substances than normal cells to use in their vital functions and thereby suffer more death and damage than normal cells.
3. Radiation—high-energy radiation that damages the DNA and proteins in cells. Cancer cells are killed and damaged at a much higher rate than normal cells due in part to their inability to repair their DNA and cell structure, their inability to rid themselves of dead and dying cells efficiently, and their high rate of metabolism.
4. Programmed Immune Cells—immune cells that have been programmed to attack only specific cancer cells.
5. Antibodies—manufactured to mark cancers for destruction by the immune system.

Surgery, chemotherapy and radiation have improved over the decades and are much more effective with fewer side effects. Accordingly, the cure and survival rate have improved substantially. The programming of immune cells and antibody treatment show great promise as well. Still 600,000 people die in the United States every year from cancer. Those who survive cancer live longer than before but suffer from varying degrees of damage and disability from the treatments. All these treatments can have a major problem. The sudden death of so many cancer cells overwhelm the disposal system of marking and digesting the dead cells. This can cause very serious cytokine reactions. This can necessitate reduction of doses, elongation of time of treatment, or cessation of treatment. This is especially true with the programmed immune cells and antibody treatments. They work almost too well. The sudden large amount of cancer or dead tissue cannot be disposed of properly and can result in a dangerous or deadly cytokine storm reaction.

General Structure of a Malignant Tumor

Solid Tumors

Solid tumors are not clones of a single cell. They are abnormal organ-like structures composed of multiple cell types and extracellular matrices. They develop through complex interactions between different components of these tissues using processes that resemble developing organs. They interact with the rest of the organism. They grow just as normal organs do but in a damaging and malignant way. They release substances to cause blood vessels and neurons to grow to and into them. They also secrete substances that suppress the host immune system. They also secrete a range of substances that cause blood clots, muscle and fat wasting to further weaken the host immune response.

Tumors of the Blood Cells

There are three main types of liquid tumors. Leukemia is defined as a clonal proliferation of hematopoietic stem cells in the bone marrow and can be broken down into 4 broad sub classifications: acute lymphoblastic, acute myelogenous, chronic lymphocytic, and chronic myelogenous. Symptoms can include fever, weight loss, and fatigue, bone pain, bleeding, and bruising. Treatment includes chemotherapy, radiation, monoclonal antibodies, or stem cell transplantation. Lymphomas are a heterogenous group of malignancies that come from the clonal proliferation of B-cell, T-cell, and natural killer cell subsets of lymphocytes. They occur at different stages of maturation. There are many different kinds of lymphomas, which are usually diagnosed by biopsy. Chemotherapy and radiation are the standard treatments for most types of lymphomas. Myeloma is a B-cell malignancy in which abnormal, clonal plasma cells proliferate and accumulate in the bone marrow. These cells disrupt normal function and invade the surrounding bone causing bone destruction. These cells typically have one or more genetic mutations responsible for immunoglobulin production. Symptoms include bone problems, confusion/mental fogginess, fatigue, frequent infections, excessive thirst, appetite and weight loss, constipation, nausea and vomiting.

Tumor Development

As tumors develop, they undergo dramatic morphological changes. They differentiate into different kinds of cells to aid tumor survival. Some develop into structural cells that include fibroblasts. These cancer-associated fibroblasts (CAF) stimulate cancer cell growth, inflammation, angiogenesis, and invasion. They also produce extracellular structural fibers, collagens, and proteoglycans that form the structural framework of the tumor. A critical step in tumor development is the recruitment of blood vessels (angiogenesis). The tumor secretes substances that make blood vessels grow to the tumor. They are not normal though. They are irregular, dilated, and often have dead ends. This results in abnormal blood flow and leaky blood vessels. The excess fluid is taken away by lymph vessels and transported back to the general circulation. Inflammatory cells also develop in tumors—other cells differentiate into different cell types just like in normal organs. For example, the myeloid cells behave differently and have different functions on the leading edge of the tumor than along blood vessels and in hypoxic areas. Monocytes promote tumor growth, invasion, and metastasis. Mast cells, neutrophils, natural killer cells, dendritic cells, and T-cells also develop, and their normal functions are corrupted to promote angiogenesis, neurogenesis, cancer cell invasion, locomotion, and metastasis. The different components of the tumor organ are not uniformly distributed within the tumors. Immune suppressive T-cells accumulate in tumors and suppress antitumor cytotoxic T-cells. Normal developing organs such as the liver have systemic functions, they produce by releasing proteins, hormones, and chemicals that aid the host. The tumor organ releases substances to aid its survival at the expense of the host. These substances can affect immunity, coagulation, and metabolism. Indeed, it is these effects that cause most cancer deaths. For example, cachexia (a syndrome of chronic wasting, fatigue, and weight loss due to the loss of adipose tissue and muscle mass) is induced by factors from the tumor. Tumors suppress the immune system resulting in increased risk of infection. Cancers also cause coagulation disorders, which are the second most common cause of death in cancers. Most deaths are from these effects and not the tumor directly.

The structure of the tumor and its micro-environment require and promote the original cancer cell to mutate and change to fit the different environment of the tumor and produce the functions it needs for survival. It functions almost like a new organ but is genetically a new evolving cellular creature with multiple differentiated cell types banding together to survive in the necessary but hostile environment of the host. This is a perversion as it eventually results in the death of the host and thereby the death of itself. Interestingly, there are two examples of contagious cancers. One is a sexually transmitted cancer among dogs. The other is a tumor among Tasmanian devils that is transmitted by biting.

What is needed is new ways to attack and prevent cancers from forming—making existing treatments more effective with less damage, and helping patient's own immune system remove these out-of-control organs from the body.

One potential target for a new way to attack cancer is the immune system's involvement in the initiation of many cancers and then in the hijacking of immune mechanisms to escape destruction by the host. The immune system seems to have a very paradoxical relationship with cancer.

Chronic low-grade inflammatory immune response can be the initiating factor in a large percentage of cancers. Chronic infections (e.g., AIDS, hepatitis B and C, etc.) account for an estimated 20% of cancer, chronic alcohol use accounts for an estimated 4%, smoking accounts for an estimated 40%, environmental factors 6%, and obesity 10%, totaling roughly 80% of cancers.

The following are additional findings related to tumor development.
1. Proper immune response can control or eliminate newly formed cancer cells.
2. Cancer-associated inflammation contributes to genetic instability, epigenetic modification, induces cancer cell proliferation, activates anti-apoptotic pathways, and stimulates angiogenesis and neurogenesis.
3. Cancer-associated neurons and internally produced neurons are inducted by the cancer to overproduce glutamate and substance P to produce a cytokine-rich environment internally and around the cancer that weaken host ability to attack the cancer.
4. In mature tumors, inflammation causes the activation of an alternate DNA repair mechanism which stabilizes the cancer genome.
5. Studies have shown that the levels of substance P and glutamate in, around and released by a tumor have a direct effect on its malignancy and ability to metastasize. Benign tumors have no excess substance P and glutamate production. They cannot invade other tissues or metastasize. The more malignant and invasive a cancer is the higher the substance P and glutamate levels in and around the cancer. There is also a straight-line increase in a cancer's ability to metastasize in relation to substance P levels. The higher the substance P level, the sooner and more likely a cancer is to metastasize. Cancers use the host's own normal immune responses, to survive the host immune responses to cancer presence.

Prevention and Treatment of Cancer Using Botulinum Toxin

By one of its mechanisms, botulinum toxin can prevent chronic low-grade inflammatory conditions. The development of cancer has been shown to be comorbid with conditions also related to chronic low-grade inflammation. These include but are not limited to depression, migraines, fibromyalgia, asthma, COPD, cirrhosis, kidney disease, IBS, diabetes acid reflux, and obesity. Subcutaneous injections of botulinum toxin have been shown in many of these conditions to stop just the overproduction of substance P and glutamate from the associated sensory ganglia (dorsal root and vagus) for 2-3 months at a time. This relieves the symptoms of the condition by blocking the overproduction of glutamate and substance P and thereby stopping chronic inflammation. Stopping the chronic inflammation should eliminate many cases of cancer from developing. Based on these facts, the use of botulinum toxin could eliminate this low-grade inflammation, preventing up to 80% of cancers.

In embodiments of the present disclosure, when a patient diagnosed with conditions caused by chronic inflammation including, but not limited to, smoking, chronic alcohol use, chronic viral infection, asbestosis, asthma, COPD, acid reflux, kidney failure, cirrhosis, diabetes, IBS or other conditions that result in chronic overproduction of substance P, which would cause chronic inflammation in the involved organs or structures of the body. If blood tests show elevated substance P or cytokine levels indicating chronic inflammation conditions, the patient may be at risk of developing cancer. The patient may be given botulinum toxin subcutaneously or by any other injection that allows the botulinum toxin to reach the unmyelinated sensory C fiber (e.g., intradermal injection, etc.) to prevent or alleviate their chronic inflammatory conditions. Blood tests to assess blood levels of substance P and glutamate may be performed to confirm that the elevated levels have returned to normal. Because the sensory innervations of internal organs originate in the vagus ganglia and spinal dorsal root ganglia, the botulinum toxin injection can be given to and/or around the vicinity of a trigeminal nerve, a cervical nerve, a thoracic nerve, a lumbar nerve, a sacral nerve, or a combination thereof of the patient. Preferably, it is not necessary to inject botulinum toxin to the vagus nerves directly because there is numerous anastomoses between the trigeminal nerves and the spinal nerves.

The selected trigeminal nerve may include, but not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve can minimize or eliminate muscular side effects. The selected cervical nerve may include, but is not limited to, the c-2 nerve, c-3 nerve, c-4 nerve, c-5 nerve, c-6 nerve, c-7 nerve, c-8 nerve, or a combination thereof. The selected thoracic nerve may include, but is not limited to, the t-1, t-2 to t-4 nerve, t-5 to t-6 nerve, t-7, t-8 to t-9 nerve, and/or t-10 to t-12 nerve, or a combination thereof. The selected lumbar nerve may include, but is not limited to, the 1-1 to 1-2 nerve, 1-2 to 1-3 nerve, and/or 1-4 to 1-5 nerve, or a combination thereof. The selected sacral nerve may include, but is not limited to, the s-1 to s-2, s-3 to s-4, and/or s-4 to s-5, or a combination thereof.

For example, 1-4 units to and/or around the vicinity of an ophthalmic, maxillary, and/or mandibular nerve of the trigeminal nerve (bilateral), 1-4 units to and/or around the vicinity of the c-2 to c-3, c-4 to c-6, and/or c-7 to c-8 of the cervical nerve, about one-inch lateral to the patient's spine (bilateral), 1-4 units to and/or around the vicinity of the t-2 to t-3, t-5 to t-6, t-7 to t-9, and/or t-10 to t-12 of the thoracic nerve, about one inch lateral to the patient's spine (bilateral), 1-4 unit to and/or around the vicinity of the 1-1 to 1-2, 1-2 to 1-3, and/or 1-4 to 1-5 of the lumbar nerve, about one inch lateral to the patient's spine (bilateral), and/or 1-4 units to and/or around the vicinity of the s-1 to s-2, s-3 to s-4, and/or s-4 to s-5 of the sacral nerve, about one inch lateral to the patient's spine (bilateral) can be administered. While the administration site is about one-inch lateral to the patient's spine in the above embodiment, the distance can be more than 0 inch, about 0.1-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. The methods according to embodiments of the present disclosure are preferably applied to all or many of these locations. Depending on symptoms or conditions, the botulinum toxin used in embodiments of the present disclosure can be injected to a subset or subgroup of the locations described in embodiments of the present disclosure. In one embodiment, 3 injections of 2 units each distributed along each side of the neck in the cervical area on the trigeminal nerve, 1 injection of 2 units in the ophthalmic, maxillary, mandibular division may be given subcutaneously and bilaterally. These dosages are for an adult who weighs about 150 lbs. The dosage for an adult or a child would have to be adjusted for age, weight, or a combination thereof.

Botulinum toxin is given to lower the levels of substance P and CGRP, and botulinum toxin to normal levels. It normally begins to work in 3-7 days.

In general, the total dosage or amount can be, for example, 1-150 units depending on the patient's body weight. Preferably, the total dosage is about 20-150 units. Preferably, the total dosage for adults whose weight is 150 lbs. is about 50-150 units. For an adult or a child, the dosage can be adjusted to the patient's body weight, age, or a combination thereof. For toddlers (e.g., from about 1 to 5 years old), the dosage can be, for example, about 1-30 units and can be adjusted to the patient's body weight and age. This is an estimate, but 30 units is the maximum dosage that has been used safely since the 1990s in cerebral palsy infants and young children to control their severe muscle spasms.

Botulinum toxin is given to lower the levels of substance P and CGRP, and botulinum toxin normally begins to work after about 3-7 days. It normally takes the botulinum toxin about one to two weeks to reach the height of its effectiveness. Blood levels of substance P and CGRP can be monitored to make sure that the levels drop to normal, and the patient's physical symptoms can be monitored to make sure the levels normalize as well. When the botulinum toxin wears off, blood tests show an increase in substance P or CGRP, and/or the symptoms begin to redevelop, more botulinum toxin can be given to combat the symptoms of the condition. For patients, as discussed, it is possible to use the method according to embodiments of the present disclosure to delay, alleviate, mitigate, or reduce the intensity, progression, or worsening of one or more attendant symptoms of a disorder or condition, and/or the method according to embodiments of the present disclosure alleviates, mitigates, or impedes one or more causes of cancer (e.g., chronic inflammatory condition).

Botulinum toxins for use according to embodiments of the present disclosure can be stored in lyophilized, vacuum dried form in containers under vacuum pressure or as stable liquids. Prior to lyophilization, the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or in the vicinity of the aforementioned nerve or to the aforementioned nerve branch or its ganglion nuclei. This method of administration permits the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of botulinum toxin within a tissue appears to be a function of dose and can be graduated. Jankovic J., et al *Therapy with Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily affects neural systems believed to be involved in a selected neuropsychiatric disorder and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor, and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

The botulinum toxin used in prevention of cancer in accordance with embodiments of the present disclosure comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, the potency, dosage, or duration may vary depend on the type of botulinum toxins. The botulinum toxin can be used with other modulating drugs or chemicals. In further embodiments, the therapeutically effective amount of the botulinum toxin administered is between about 1 unit and about 150 units. The therapeutically effective amount can be about 1 to about 50 units, about 1 to about 30 units, about 50 to about 100 units, about 1 to about 60, about 6 to about 60, and about 50 to about 150.

In some embodiments, a composition administered to a patient consists of botulinum toxin(s). Alternatively, a pharmaceutically active composition contained in a composition administered to a patient consists of botulinum toxin(s). The composition may additionally include, but not be limited to, a pharmaceutically inactive excipient, stabilizer and/or carrier. The composition may further comprise one or more additional pharmaceutically inactive ingredients. If lyophilized, the botulinum toxin may be reconstituted with saline or water to make a solution or composition to be administered to the patient. Alternatively, a composition administered to a patient comprises botulinum toxin(s) and other pharmaceutically active ingredients.

In some embodiments, a composition administered to a patient consists of nitrous oxide and oxygen.

In some embodiments, a pharmaceutically active composition contained in a composition administered to a patient consists of nitrous oxide and oxygen.

The composition may additionally include a pharmaceutically inactive composition such as a pharmaceutically inactive excipient, stabilizer and/or carrier.

Unless defined otherwise, all technical and scientific terms used herein have same meaning as commonly understood by the person of ordinary skill in the art to which this disclosure belongs.

Novel Location and Injection Techniques to Mitigate or Eliminate Muscular Side Effects of Botulinum Toxin While Controlling the Overproduction of Substance P, Glutamate, and CGRP 1. Subcutaneous Injection The subcutaneous injections allow for the botulinum toxin to diffuse into the unmyelinated C-fibers and pass by diffusion up to the ganglia where it renders nonfunctional the SNAP-25 protein in the neurostructural cells (astrocyte, glial, and satellite). This blocks the release of substance P, glutamate, and CGRP into the spinal fluid surrounding the neuron. This mechanism blocks only the overproduction of substance P and glutamate while not interfering with the normal production and use of these vital neurotransmitters. Neurons have receptors on their surfaces that are activated by substance P, glutamate, and CGRP. Immune cells have substance P receptors (NKI-3) that activates immune cells to produce cytokines. With intramuscular injections, the botulinum toxin must diffuse through the muscle, fibrous tissue, and myelin to reach the motor neuron and block the acetylcholine. The unmyelinated C-fibers in the skin allow the botulinum toxin to diffuse into the neuron more efficiently than myelin protected neurons in the muscles and at a much lower dose due to ease of diffusion.

2. Injection Site ½ Inch Lateral to the Spine

When the botulinum toxin is given subcutaneously, it must diffuse up the C-fiber axon by passive diffusion. This is a very slow process, and the botulinum toxin can degrade on the journey. Early trials using botulinum toxin for the treatment of fibromyalgia used 25 units per injection given over trigger points in the forearm and calf. This covered only the injected dermatomes and took 2-3 weeks to diffuse up the axon and reach the ganglia. This problem can be addressed by giving the subcutaneous injections approximately ½ inch lateral to the spine. The site of excess substance P, glutamate and CGRP is in the neuro structural cells of the dorsal root and vagal sensory ganglia. The botulinum toxin must only diffuse approximately 1 inch rather than several feet. This allowed us to use only 1-2 units of botulinum toxin; and diffusion time is 3-5 days. Due to anastomosis among the spinal sensory nerves in this area, this injection technique covers 2-3 dermatomes. The shorter time and distance also allow for less time for degradation of the botulinum toxin.

3. Vagus Nerve Injection

The Vagus nerve is a spinal nerve that exits the base of the skull and travels down the throat to the internal organ it supplies (parasympathetic, motor, and sympathetic innervations to the throat and internal organs). The vagus nerve's only superficial innervations are a nerve called Arnold's nerve that innervates the skin in the external ear. At this location it is a mixed motor and sensory nerve. The motor component innervates the throat muscles. Injection in this area could cause muscle weakness or paralysis in the throat. Studies show that there are numerous anastomoses between the trigeminal and cervical sensory nerves and the vagus sensory nerves. Subcutaneous botulinum toxin injection in the trigeminal and cervical dermatomes allows for diffusion through these anastomoses to the sensory vagal nerves to reach the sensory vagal ganglia with botulinum toxin and prevent the overproduction of only substance P, glutamate, and CGRP. This minimizes or eliminates vagal nerve motor side effects. This also eliminates the complicated and potentially dangerous injections directly to the vagus ganglia.

4. Mitigated or Eliminated Spinal Motor Side Effect

The injection location approximately ½ inch lateral to the spine is the only location in the body where the sensory and motor systems are truly separated. In the spinal cord, the motor and sensory nerves are in very close proximity; however, when they exit the spinal column, the sensory nerves exit in the dorsal root, and the motor nerves exit in the ventral root. Then lateral to the spine, they unite and form a mixed nerve. At this injection point ½ inch lateral to the spine, the sensory nerves are separated by bones and connective tissues preventing diffusion to the motor nerves in the ventral root, thereby mitigating or eliminating motor side effects.

5. Summation

The injection techniques allows the botulinum toxin to reach all the sensory dermatomes if needed. This prevents the neurostructural cells of the sensory ganglia from chronically overproducing substance P, glutamate, and CGRP without affecting normal intra-neuron production and function of these compounds. These techniques allow treatment of conditions that are caused by excess substance P, glutamate, and CGRP with minimal or no muscular side effects. The approximate 60 units needed to be effective by these techniques is far below the maximum botulinum toxin unit limit of 400 units. The mechanism of action of botulinum toxin combined with the novel injecting techniques should allow for safe control of chronic inflammatory conditions. This control should eliminate the initiating factors that lead to cancerous changes in cells.

Treatment of the Conditions or Symptoms Associated with Cancers from Acute Elevations of Substance P and Glutamate The conditions or symptoms may include, but not limited to:

1) Acute pain associated with some cancer.
2) Internal tumor production of cytokines that protects the tumor from host immune response and causes hypertensive and hypoxic environment that prevent diffusion of chemotherapy into the tumor.
3) Production and release of cytokines from the tumor that damage the host. These cytokine cause blood clots, suppress host immune system, cause muscle and fat wasting, depression, etc.
4) Limitation of type, dosage, duration, of existing treatments due to large amounts of dead cancer cells triggering severe cytokine production.
5) Extreme cytokine levels increasing malignancy and the ability of concerns to metastasize.

The following mechanisms contribute to the malignancy, ability to metastasize and suppression of the host immune system.

The half-life of most cytokines is seconds to minutes. The cells that produce them must be constantly stimulated to produce them. One of these tachykinins, substance P, has been shown to be a major pro inflammatory mediator. Glutamate has been shown to cause, among other things, neuropathic pain, depression, sleep disturbances, anxiety.

The biggest threat to the existence of cancer is the host's immune system. Numerous mechanisms exist to detect, neutralize, or destroy cancer cells and tumors. Millions of cells develop cancer-like characteristics every day, and they either go into apoptosis or are marked for destruction by the immune system.

If a cancerous cell escapes destruction by apoptosis or the immune system and begins to proliferate, it uses the host's own immune system to evade destruction. By a process of neurogenesis, the tumor induces nerves in its vicinity to proliferate and grow to it. Some cancers can cause internal stem cells to develop into neurons. The cancer cell then stimulates these neurons to produce extremely high levels of substance P, and glutamate. The extreme glutamate released into the surrounding tissues and blood causes severe neuropathic pain, sleep disturbances, anxiety, and depression.

The elevated level of substance P inside and around the tumor triggers high cytokine storm type levels of cytokines in and around the cancer that do two things. They cause acute levels of cytokine inflammation, which is part of the reason there is elevated fluid and pressure levels in the tumor. The pressure prevents proper absorption of the chemotherapy agents from the blood. It is estimated that in some cases, the level of chemotherapy agent in the tumor is only 2-3% of the blood level. The excess cytokines in and around the cancer also protect it from the host immune system. The cancer cells evolve to where they can survive in the cytokine-rich environment. The tumor-produced cytokines not only act as a barrier to immune cells around the tumor but also spill into the circulatory system and damage the host. Some of the effects of this are (1) generalized suppression of the immune system, (2) chronic wasting of the muscles and fat, (3) fatigue, (4) blood clots, (5) depression, and (6) increased risk of infection. This weakens the host and reduces its ability to fight the cancer.

Normally when cells die, become defective, have cancer-like properties, or age-related degeneration, they are marked by a protein called protein S which attract macrophages called phagocytes that engulf and digest the defective cells, cellular debris, dead bacteria, viruses, and blood clots. A major problem during chemotherapy, radiation therapy, or infusion of chimeric antigen receptor (CAR) T lymphocytes, occurs when too much cancerous tissue is destroyed too quickly for the debris removal process. The destroyed cells lyse, and the toxic substances irritate and damage the surrounding tissues. Among the cells damaged are sensory nerves. The large amount of dead tissues invoke an acute and significant overproduction of substance P and glutamate with the resulting severe and potentially deadly cytokine storm. This is one of the reasons many cancer treatments must be done with lower doses over longer periods of time. This is especially true with the CAR T targeted lymphocyte treatment. It is a particular true with children under this treatment. Sometimes, treatments must be discontinued due to the complication induced by the cytokine storm.

The use of nitrous oxide should be able to mitigate or eliminate these cytokine-induced systemic effects, remove the cytokine shield around the tumor to allow the immune system to better attack the tumor, allow current treatment to be more effective, decrease the malignancy and ability of a tumor to metastasize, and mitigate extreme pain associated with some cancer.

The Use of Nitrous Oxide to Lower the Ganglia Acute Overproduction of Substance P in Cancer Nitrous oxide may be used to suppress the neural controlled production of substance P at dosages that do not cause over-sedation, respiratory depression, irritation of the lungs, or other side effects. The inhaled dosage can be from about 1% nitrous oxide/about 99% oxygen to about 70% nitrous oxide/about 30% oxygen depending on individual needs and sensitivity. Clinical indications suggest that about 40% nitrous oxide/about 60% oxygen to about 50% nitrous oxide/about 50% oxygen would be optimal. Other aforementioned inhaled anesthetics may be included in the dosage or only the specified composition may be used.

Time of inhalation would vary from one minute to continuous with about 20-30 minutes being the optimal time frame. Duration of substance P suppression can be from about 1 minute to about 12 hours with average cases of about 4-6 hours of substance P suppression. Depending on the level of substance P, the nitrous oxide and oxygen may be administered to a patient before, during, and/or after cancer occurs between about for about 1 minute to about 12 hours every about 4-6 hours and optionally with continuous administration over the period of time. Total duration of treatment will be until cancer is mitigated or controlled by the proper treatment. The nitrous oxide mechanism is suppression of substance P in the spinal and vagal sensory ganglia. The amount of nitrous oxide used, duration of administration, and length of effectiveness can be adjusted to the individual. The time needed to control the cytokine reaction and the % nitrous oxide/oxygen ratio will vary. The time of each administration, the length of time between each treatment, and the duration of each treatment will provide medical practitioners with a very flexible tool to control these acute cytokine reactions. In some embodiments, the nitrous oxide treatment will need to be used before and/or while the cancer is treated and may be used for any post treatment chronic inflammatory conditions that result from the treatment. The only major side effect to longer term nitrous oxide treatment is folic acid deficiency. Supplemental folic acid during the treatment should be able to alleviate the potential problem. For children, adjustments will have to be made for age and body weight. The dosing of other inhaled anesthetics in relation to oxygen and time may vary from nitrous oxide. Other inhaled anesthetics may have to be used at a different oxygen % than the nitrous oxide to produce effective clinical results. Other aforementioned inhaled anesthetics can be included in the dosage or only the specified composition can be used. Other inhalants can be included in the above-compositions such as for other purposes.

Substance P-induced inflammation levels and glutamate levels are directly related to the malignancy and ability to metastasize of a cancer. It is a straight-line ability. Benign tumors have no excess glutamate and substance P with their resulting inflammation and cytokine production. The higher the levels of the two tachykinins are, the more malignancy and the higher rates of metastasis. The nitrous oxide should mitigate or eliminate these cancer characteristics. Studies have shown that glutamate and substance P antagonists may improve the results of chemotherapy in vitro. However, they can only be used in limited doses in vitro since substance P and glutamate function as vital neurotransmitters. Regarding glutamate-induced pain, the more severe the pain, the more aggressive the tumor growth. Drugs that affect the pain (bupivacaine and morphine) may suppress tumor growth.

If side effects from too much substance P suppression nitrous oxide use occur, then inhalation may be reduced or eliminated. Before, during, and after the provision of the inhaled nitrous oxide and oxygen, blood tests may be done to monitor and assess the patient's cytokine level including a substance P level and a viral load. In addition, before, during and after the inhalation of nitrous oxide and oxygen, a blood oxygen level and a pulse may be monitored and assessed.

In some instances, the therapeutically effective amount of botulinum toxin can be about 1 (or 2) to about 4 units.

Case Study

The following is a case study of a 59-year-old female who weighs about 150 lbs. She was diagnosed with chronic myeloid leukemia. She took Sprycel 50 g daily for chemotherapy, which controlled her leukemia but did not cure it. The cancer gave her extreme, chronic cancer pain all the time. She takes oxycodone every 6 hours, fentanyl patch 25 grams every 3 days, and pregabalin twice a day. The medications did not relieve her pain but just took the edge off.

She has had 5 dental appointments since her cancer had started. At her dental appointments, she was given 50% nitrous oxide/50% oxygen by inhalation for appointments 30 minutes each visit for her dental anxiety. Within minutes of the administration of the nitrous oxide her severe pain was completely gone. After her appointment, the central sedation was gone within minutes, and she was capable of driving. Her pain was completely gone for 6-8 hours, which indicates that nitrous oxide can suppress these acute levels of glutamate and substance P in cancers. This ability should also mitigate the pathogenicity of cancers and make them easier to treat with conventional treatments and allow the host immune system to attack the cancer more successfully.

Further patient testing is being pursued using botulinum toxin and nitrous oxide.

Conclusion

Subcutaneous botulinum toxin should be able to suppress the chronic inflammation which is thought to be responsible for a large percentage of cancer, thereby preventing the cancer development. Blood tests can be done to detect higher than normal levels of substance P and glutamate and neuropathic conditions can be evaluated, or if a patient has conditions caused by chronic inflammation.

Nitrous oxide suppression of ganglia produced acute levels of substance P and glutamate should benefit cancer treatment by stopping or mitigating the cytokine-induced storm during treatments. It should reduce the cytokine shield around tumors, allowing the body's immune system to attack the cancer. It should also lower the pressure gradient inside the tumor to allow for more chemotherapy to reach the cancer. It will also mitigate or stop the release of cytokines from the cancers that cause blood clots, suppress host immunity, and cause muscle and fat degradation that are a major source of death in cancer patients, and mitigate the extreme pain of some cancers. It should also mitigate and suppress cancer malignancy and its ability to metastasize. It can also be used to help post cancer conditions such as but not limited to, migraines, neuropathic pain, memory impairment, shortness of breath, or other breathing issues, diabetes, etc. These are caused by chronic cytokine production brought about by the treatment injury to normal tissue.

The description of ranges also describes the ranges within the specifically described range and describes individual numerical points for treatment. The described ranges are inclusive of endpoints in the range.

It should be understood that the present description of embodiments of the invention includes a composition for use in treating the conditions. For example, botulinum toxin for use in treating cancer in a patient in a need thereof.

It should be understood that the above description of the disclosure and specific examples, while indicating preferred embodiments of the present disclosure, are given by way of illustration and not limitation. Many changes and modifications within the scope of the present disclosure may be made without departing from the spirit thereof, and the present disclosure includes all such changes and modifications.

What is claimed is:

1. A method of treating cancer and/or post-cancer symptoms or conditions in a patient in need thereof, wherein the patient has a physiological state comprising overproduction of substance P and/or glutamate and related cytokine overproduction protecting malignant cancer cells, the method comprising:
   administering nitrous oxide and oxygen to the patient by inhalation, thereby treating the cancer and/or post-cancer treatment symptoms or conditions,
   wherein when administered to an adult who weighs about 150 lbs., the nitrous oxide and oxygen are administered for about between 1 minute and about 1 hour every about 4-6 hours; or for about 20 minutes every about 4-6 hours; and
   providing the patient with cancer treatment.

2. The method of claim 1, wherein the nitrous oxide and oxygen comprises from about 1% nitrous oxide/about 99% oxygen to about 70% nitrous oxide/about 30% oxygen; from about 40% nitrous oxide/about 60% oxygen to about 50% nitrous oxide/about 50% oxygen; or about 50% nitrous oxide/about 50% oxygen.

3. The method of claim 1, wherein the nitrous oxide and oxygen are administered by continuous administration over the period of time of 1 minute and about 1 hour.

4. The method of claim 1, wherein a composition, duration, an interval, and a total amount of the nitrous oxide and oxygen provided to an adult or a child is adjusted for age, weight, or a combination thereof.

5. The method of claim 4, the cancer treatment comprises one or more of the following: surgery, chemotherapy, radiation, programmed immune cells, and antibodies.

6. The method of claim 4, the method further comprising monitoring glutamate and Substance P suppression and in response, modifying the administration of nitrous oxide and oxygen by inhalation.

7. The method of claim 4, the method further comprising administering folic acid to the patient.

* * * * *